United States Patent
Insinna et al.

(10) Patent No.: US 11,931,048 B2
(45) Date of Patent: Mar. 19, 2024

(54) CUTTING GUIDE FOR SPINAL OSTEOTOMY

(71) Applicant: MEDACTA INTERNATIONAL SA, Castel San Pietro (CH)

(72) Inventors: Yuri Insinna, Castel San Pietro (CH); Meinrad Fiechter, Castel San Pietro (CH); Francesco Siccardi, Castel San Pietro (CH)

(73) Assignee: Medacta International SA, Castel San Pietro (CH)

( * ) Notice: Subject to any disclaimer, the term of this patent is extended or adjusted under 35 U.S.C. 154(b) by 438 days.

(21) Appl. No.: 17/428,266

(22) PCT Filed: Nov. 26, 2019

(86) PCT No.: PCT/IB2019/060161
§ 371 (c)(1),
(2) Date: Aug. 3, 2021

(87) PCT Pub. No.: WO2020/170021
PCT Pub. Date: Aug. 27, 2020

(65) Prior Publication Data
US 2022/0104832 A1 Apr. 7, 2022

(30) Foreign Application Priority Data
Feb. 22, 2019 (IT) .......................... 102019000002575

(51) Int. Cl.
*A61B 17/15* (2006.01)
*A61B 17/17* (2006.01)
*A61B 17/56* (2006.01)

(52) U.S. Cl.
CPC ........ *A61B 17/152* (2013.01); *A61B 17/1757* (2013.01); *A61B 17/56* (2013.01); *A61B 2017/568* (2013.01)

(58) Field of Classification Search
CPC .......................... A61B 17/152; A61B 17/1757
See application file for complete search history.

(56) References Cited

U.S. PATENT DOCUMENTS

| 5,112,337 A | 5/1992 | Palous et al. |
| 5,843,085 A | 12/1998 | Graser |

(Continued)

FOREIGN PATENT DOCUMENTS

| CN | 206560458 | 10/2017 |
| DE | 4219939 A1 | 12/1993 |

(Continued)

OTHER PUBLICATIONS

Berry et al., Personalised image-based templates for intra-operative guidance, Proceedings of the Institution of Mechanical Engineers, Part H: Journal of Engineering in Medicine, vol. 219, pp. 111-118, 2004.

(Continued)

*Primary Examiner* — Christian A Sevilla
(74) *Attorney, Agent, or Firm* — Meunier Carlin & Curfman LLC

(57) ABSTRACT

A cutting guide for spinal osteotomy comprises a main body having a first and a second arm, each provided with a respective through slot. The first and second arm are preferably inclined with respect to each other to substantially form a V shape. The guide also comprises a distal surface and a proximal surface shaped according to the anatomy of the specific patient and a height of each arm is also shaped according to the anatomy of the specific patient.

12 Claims, 7 Drawing Sheets

(56) References Cited

U.S. PATENT DOCUMENTS

| | | | |
|---|---|---|---|
| 5,928,232 | A | 7/1999 | Howland et al. |
| 6,007,537 | A | 12/1999 | Burkinshaw et al. |
| 8,758,357 | B2 | 6/2014 | Frey |
| 8,870,889 | B2 | 10/2014 | Frey |
| 9,198,678 | B2 | 12/2015 | Frey et al. |
| 9,642,633 | B2 | 5/2017 | Frey et al. |
| 9,987,024 | B2 | 6/2018 | Frey et al. |
| 2002/0123668 | A1 | 9/2002 | Ritland |
| 2007/0066977 | A1 | 3/2007 | Assell et al. |
| 2008/0114370 | A1 | 5/2008 | Schoenefeld |
| 2008/0243257 | A1* | 10/2008 | Taber .................. A61B 17/152 606/88 |
| 2008/0262500 | A1* | 10/2008 | Collazo ............. A61B 17/8095 606/88 |
| 2008/0287954 | A1* | 11/2008 | Kunz ................ A61B 17/1764 606/87 |
| 2008/0294170 | A1* | 11/2008 | O'Brien ............... A61B 17/152 606/87 |
| 2009/0024132 | A1 | 1/2009 | Blain et al. |
| 2009/0088763 | A1* | 4/2009 | Aram .................. A61B 17/157 606/88 |
| 2010/0023018 | A1 | 1/2010 | Theofilos |
| 2011/0319745 | A1 | 12/2011 | Frey |
| 2012/0053590 | A1 | 3/2012 | Allen et al. |
| 2012/0130382 | A1 | 5/2012 | Iannotti et al. |
| 2012/0245587 | A1 | 9/2012 | Fang et al. |
| 2013/0053854 | A1 | 2/2013 | Schoenefeld et al. |
| 2013/0123850 | A1 | 5/2013 | Schoenefeld et al. |
| 2013/0218163 | A1 | 8/2013 | Frey |
| 2014/0074099 | A1 | 3/2014 | Vigneron et al. |
| 2014/0163565 | A1 | 6/2014 | Bollinger |
| 2014/0200618 | A1 | 7/2014 | Donner et al. |
| 2014/0277460 | A1 | 9/2014 | Schifano et al. |
| 2014/0350614 | A1* | 11/2014 | Frey ...................... A61B 34/10 606/86 R |
| 2014/0358152 | A1 | 12/2014 | Condino et al. |
| 2015/0320430 | A1 | 11/2015 | Kehres et al. |
| 2018/0042619 | A1 | 2/2018 | Frey et al. |
| 2018/0177512 | A1 | 6/2018 | Hogan et al. |
| 2018/0296254 | A1 | 10/2018 | Tsai et al. |
| 2021/0077119 | A1 | 3/2021 | Siccardi et al. |
| 2021/0077130 | A1 | 3/2021 | Siccardi et al. |

FOREIGN PATENT DOCUMENTS

| | | |
|---|---|---|
| DE | 102016218965 A1 | 4/2018 |
| EP | 2502582 A1 | 9/2012 |
| EP | 2749235 A1 | 7/2014 |
| JP | 2015208566 | 11/2015 |
| JP | 2016524506 B2 | 8/2016 |
| TW | 200908927 A | 3/2009 |
| TW | 201238556 A | 10/2012 |
| WO | 9600049 A1 | 1/1996 |
| WO | 2012156466 | 11/2012 |
| WO | 2013158521 A1 | 10/2013 |
| WO | 2014070889 A1 | 5/2014 |
| WO | 2014090908 A1 | 6/2014 |
| WO | 2014197844 A1 | 12/2014 |
| WO | 2016075581 A1 | 5/2016 |
| WO | 2016075660 A1 | 5/2016 |
| WO | 2018055494 A1 | 3/2018 |
| WO | 2018055518 A1 | 3/2018 |
| WO | 2019123192 A1 | 6/2019 |
| WO | 2019123193 A1 | 6/2019 |

OTHER PUBLICATIONS

Brussel et al., Medical Image-Based Design of an Individualized Surgical Guide for Pedicle Screw Insertion, 18th Annual International Conference of the IEEE Engineering in Medicine and Biology Society, Amsterdam, pp. 225-226, 1996.

Lu et al., A novel computer-assisted drill guide template for placement of C2 laminar screws, Eur Spine J, vol. 18, pp. 1379-1385, 2009.

Lu et al., A Novel Patient-Specific Navigational Template for Cervical Pedicle Screw Placement. SPINE, vol. 34, No. 26, pp. E959-E964, 2009.

Lu et al., Rapid prototyping drill guide template for lumbar pedicle screw placement, Chinese Journal of Traumatology, vol. 12(3), pp. 171-177, 2009.

Popescu et al., Design and Rapid Manufacturing Of Patient-Specific Spinal Surgical Guides: A Survey, Proceedings in Manufacturing Systems, vol. 7, Issue 2, pp. 115-120, 2012.

Radermacher, Klaus, Computer Assisted Orthopaedic Surgery with Individual Templates, Helmholtz-Institute for Biomedical Engineering, 2 pages, 1997.

Ryken et al., Image-based drill templates for cervical pedicle screw placement, J Neurosurg Spine vol. 10, pp. 21-26, 2009.

English Translation of Notice of Reasons of Refusal in JP 2019-536354, dated Feb. 10, 2020, 7 pages.

International Search Report and Written Opinion issued for Application No. PCT/IB2017/055688, dated Nov. 16, 2017. 11 pages.

International Search Report and Written Opinion issued for Application No. PCT/IB2017/055588, dated Nov. 22, 2017. 13 pages.

English Translation of Notice of Reasons of Refusal in JP 2019-536348, dated Feb. 27, 2020, 14 pages.

International Search Report and Written Opinion issued for Application No. PCT/IB2019/053765 dated Aug. 6, 2019, 15 pages.

International Search Report and Written Opinion for International Application No. PCT/IB2019/058162 dated Jan. 22, 2020, 16 pages.

Office Action issued for U.S. Appl. No. 16/333,057, dated Jul. 30, 2020.

Office Action issued for U.S. Appl. No. 16/333,055, dated Dec. 8, 2020.

International Search Report and Written Opinion, issued by the International Searching Authority (ISA/EP) in PCT Application No. PCT/IB2019/060161 dated Apr. 2, 2020. 11 pages.

Notice of Reasons of Refusal received in JP 2021-549497 with English Translation, dated Oct. 17, 2022, 9 pages.

Notice of Allowance received in connection with U.S. Appl. No. 16/956,253, dated Feb. 8, 2022, 10 pages.

Notice of Allowance in U.S. Appl. No. 17/055,643, dated May 30, 2023, 7 pages.

Office Action for U.S. Appl. No. 16/956,250, dated May 2, 2022, (32 pages).

International Search Report and Written Opinion, issued by the International Searching Authority (ISA/EP) in Application No. PCT/IB2018/060161 dated Apr. 5, 2019. 9 pages.

International Search Report and Written Opinion, issued by the International Searching Authority (ISA/EP) in Application No. PCT/IB2018/060160 dated Apr. 5, 2019. 13 pages.

Office Action issued for U.S. Appl. No. 16/956,253, dated Oct. 12, 2021.

Office Action issued for U.S. Appl. No. 17/281,900 dated Dec. 2, 2021.

* cited by examiner

CUTTING GUIDE FOR SPINAL OSTEOTOMY

TECHNICAL FIELD

The present invention relates to a cutting guide for spinal osteotomy.

In case of spinal deformations such as kyphosis and scoliosis or degenerative diseases such as neurofibromatosis, the patient has an unnatural curvature of the spine with a collapse between the various vertebrae. Therefore, there is no more intradiscal space with consequent deformation of the patient's posture and compression of the spinal cord. When it is necessary to straighten the spine, a portion of the vertebral column must be removed and the vertebrae must be forced to assume the correct anatomical shape.

Prior Art

Usually the operation consists in cutting a wedge-shaped portion of the vertebrae by operating on two or more vertebrae to create a space that allows the straightening of the vertebral column.

The stiffening bars are then positioned and secured with special screws.

Currently, osteotomy cuts are made free hand without the aid of tools to guide the cutting blade; as a result, the cuts may not be precise, although they can be planned on x-ray or CT before surgery.

Another difficulty of the current surgical technique consists in identifying the correct depth of incision for the cut, which must arrive near the medullary canal. The vertebral bone structure is, therefore, not completely severed but the last portion of the bone is broken by hand.

This is to avoid a complete cut's affecting the medullary canal with consequent damage to the patient.

The front part of the vertebra(e) is removed free hand, using the planes created by the removal of the back part as a reference.

In addition, a further complication of the current surgical technique is the inclination of the cutting planes, which are not always easy to identify intra-operatively.

In fact, there are no navigation systems to perform osteotomies on the vertebral column that provide the surgeon with a precise and safe reference for the line and depth of incision.

The purpose of the present invention is to overcome the drawbacks of the prior art.

In particular, the purpose of the present invention is to propose a patient-specific cutting guide for spinal osteotomy.

Another purpose of the present invention is to create a cutting guide for spinal osteotomy that precisely identifies the planes along which the surgeon must perform the cutting of the vertebrae, thus facilitating the surgical operation itself as well as ensuring greater safety for the patient. The purpose of the present invention is also to provide a cutting guide for spinal osteotomy that is able to define a pre-defined cutting depth that ensures the exact depth of incision, avoiding the risk of damage to the medullary canal.

These and other purposes and advantages are achieved by a cutting guide for spinal osteotomy as described in the attached claims.

SUMMARY

A first aspect of the present invention involves a cutting guide for spinal osteotomy, which comprises a main body having a first and a second arm, each provided with a respective through slot. The slots preferably define a V and meet at a vertex. The cutting guide is patient-specific and, therefore, comprises a distal and proximal surface that are shaped according to the anatomy of the specific patient.

In a second aspect, the cutting guide according to the present invention is characterized in that it also has a height shaped to the anatomy of the specific patient. This determines the precise cutting depth to avoid affecting the medullary canal.

Advantageously, the first arm, facing in the cranial direction considered in use configuration, and the second arm, facing in the caudal direction considered in use configuration, extend along a main longitudinal development direction along their respective axes of symmetry, which are substantially horizontal, inclined with respect to each other and intersecting, said axes of symmetry, at a vertex, placed laterally with respect to the spine.

The slots in each arm extend along the longitudinal axes of the respective arms.

The slots, advantageously, have through planes across their longitudinal extension, therefore, across the longitudinal axes of the arms, which intersect at the intersection vertex of the axes of symmetry. In addition, these through planes may converge in the proximal direction, therefore, they intersect along a line below the vertebral column considering the patient in a prone position or contained in the volume of the vertebral column. A third configuration of the arms involves these planes intersecting both laterally to the vertebral column and below the vertebral column.

Advantageously, the cutting guide has a triangular plan shape. In other words, the cutting guide, according to the present invention, comprises at least three supporting feet, one at each arm and one near the vertex. This allows a better and uniform distribution of the loads exerted by the surgeon's pressure on the vertebrae.

The cutting guide also comprises a gripping and positioning element. Advantageously, this gripping and positioning element is interposed between the first and second arm.

In addition, the cutting guide comprises a connecting bridge between the two above-mentioned arms, at which the gripping and positioning element is made. This connecting bridge can also have a triangular shape with a vertex positioned at the gripping element, so as to facilitate the uniform distribution of the loads applied to the gripping element.

BRIEF DESCRIPTION OF THE FIGURES

A cutting guide for spinal osteotomy as described and claimed is also shown in the following figures that are intended to be illustrative and not exhaustive, wherein:

DETAILED DESCRIPTION

Figure 1:
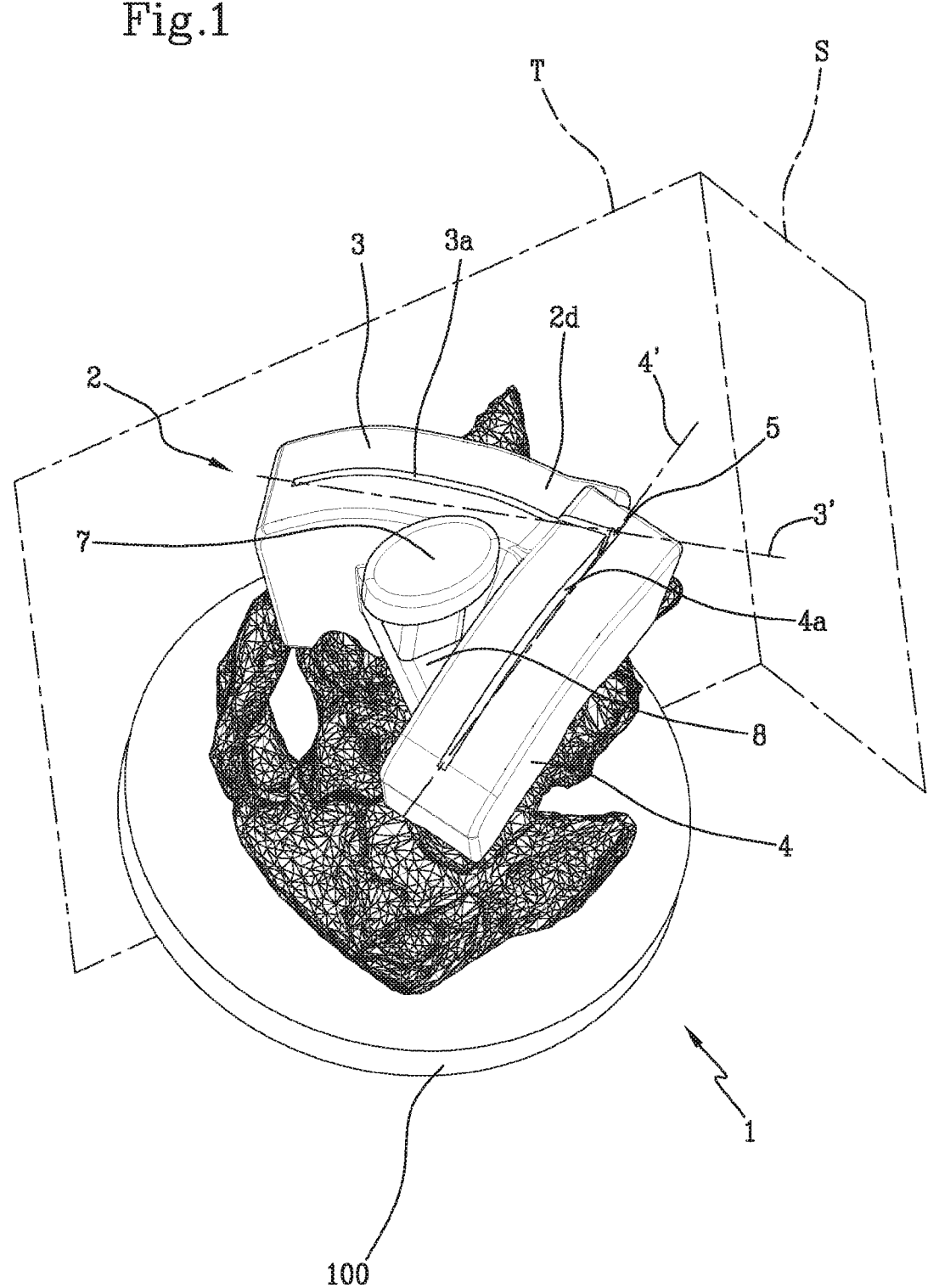
FIG. 1 is a perspective view of a cutting guide for spinal osteotomy, according to the present invention, joined to a vertebra to be sectioned.

In the accompanying figures, the number 1 indicates a cutting guide for spinal osteotomy, in accordance with the present invention.

This guide 1 comprising a main body 2 having a distal surface 2d and an opposite proximal surface 2p, where the terms distal and proximal refer to a patient placed in a prone position.

The main body 2 also comprises a first 3 and a second 4 arm, each provided with a respective through slot 3a and 4a, joining the distal surface 2d and the proximal surface 2p.

The first arm 3 is preferably facing in the cranial direction, considered in use configuration, while the second arm 4 is facing in the caudal direction, again, considered use configuration. Both the arms 3 and 4 extend along a respective main longitudinal development direction along respective axes of symmetry 3' and 4'.

Depending on the degree of deformity and on the curvature of the spine, the arms may be parallel with respect to each other and parallel to a transverse plane T considering the patient in a prone position, or they may be more or less inclined to each other and with respect to the transverse plane T and/or sagittal plane S and/or frontal plane F. In some situations, the inclination of the arms may even define a V shape, as shown in the attached FIGS. 1-5. Therefore, the longitudinal axes of symmetry 3' and 4', along which the first 3 and the second 4 arms develop respectively, are parallel with respect to each other or inclined to each other and intersecting at a vertex placed on one side of the vertebral column.

Figure 6:
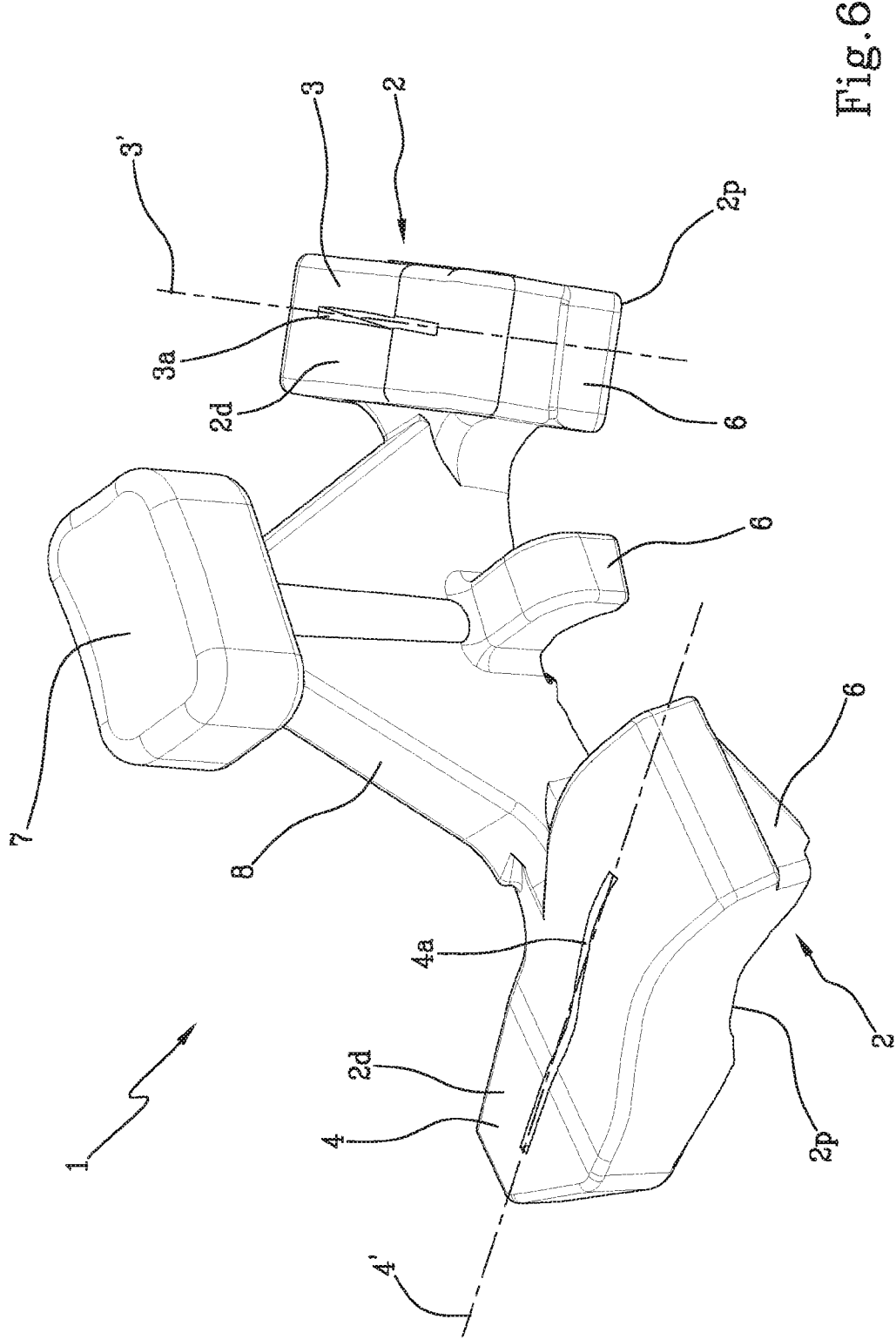
FIGS. 6 and 7 show an alternative configuration of the guide that is the subject of the present invention.
Figure 7:
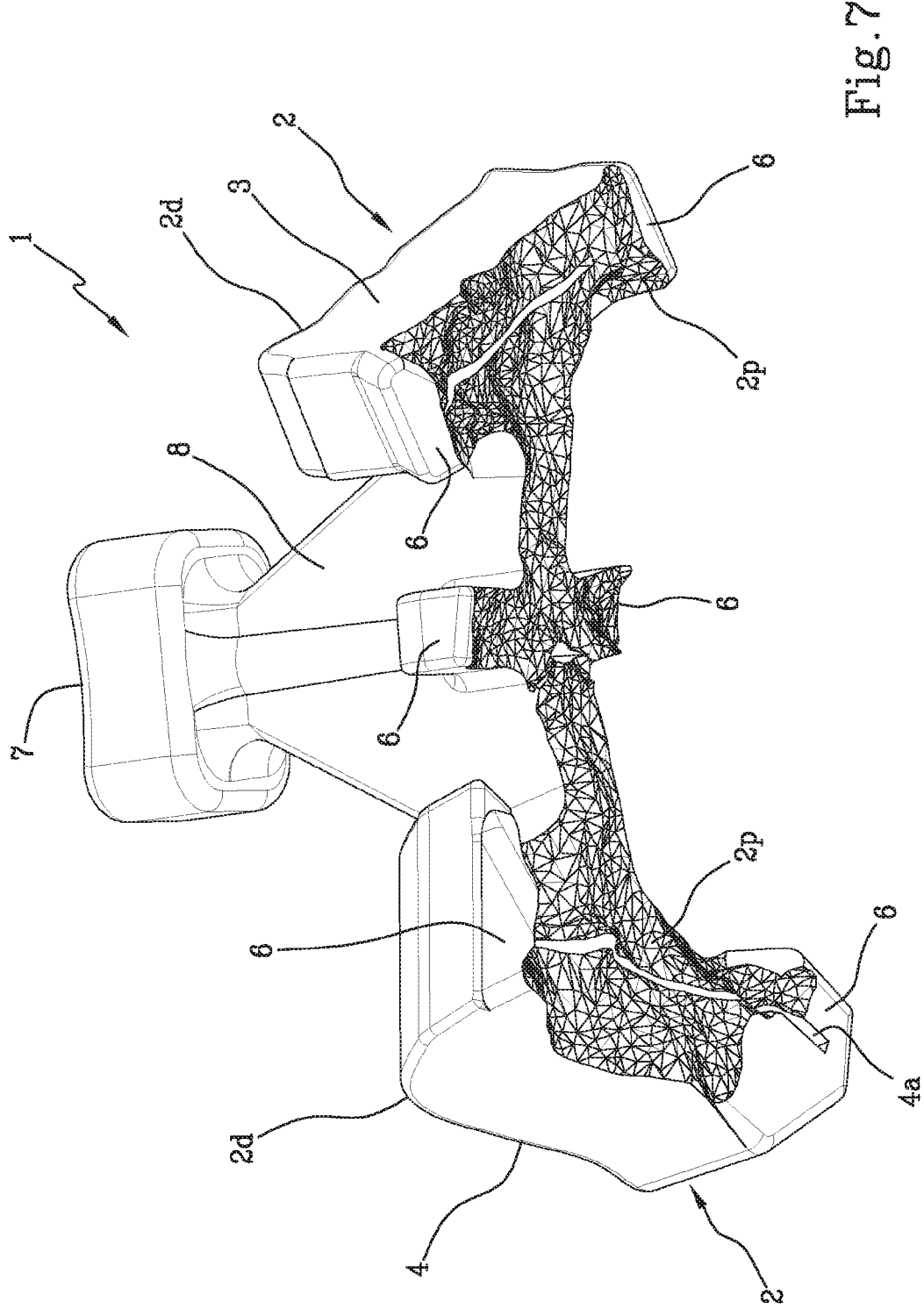

Consequently, the slots 3a and 4a are also parallel with respect to each other or more or less inclined to each other and with respect to the transverse plane T and/or sagittal plane S and/or frontal plane F, until they define a V shape, joining at a vertex 5, as shown in the attached FIGS. 1-5. The arms can be slightly inclined with respect to each other and not define a genuine convergent V in a vertex, as shown in FIGS. 6 and 7.

As a result of the unnatural curvature of the vertebral column, the portion of vertebrae to be removed must, advantageously, be wedge-shaped so that the vertebral column can subsequently be straightened by bringing the two exposed surfaces of the sectioned vertebrae into contact or proximity.

The width of the slots is such that it adapts to the size of the blade of the cutting tool that is used.

The length, on the other hand, depends on the size of the guide, which is shaped according to the anatomy of the specific patient.

In particular, the distal surface 2d and the proximal surface 2p are shaped according to the anatomy of the specific patient.

The height or thickness h of the cutting guide 1 is also designed according to the anatomy of the specific patient and follows the course of the deformed vertebrae to be removed.

The most delicate and problematic step of the cutting operation consists in precisely and safely severing the vertebrae according to a predefined cutting line, so as to remove the correct portion of vertebrae in order to straighten the vertebral column according to a natural course and restore the correct anatomy.

Even more delicate is the establishing, with absolute precision, the cutting depth that must reach near the medullary canal without, however, affecting it.

For this reason, the height h of the cutting guide 1, i.e. the distance between the distal surface 2d and the proximal surface 2p, is also shaped according to the specific patient.

The resection tools, in fact, are standard and have predefined lengths: the sum of the thickness of the vertebrae 100, evaluated during the preoperative step, and of the height of the guide must be such as to allow the blade to cut the vertebra up to a depth of a few millimetres away from the top of the medullar canal. A small thickness of bone is then left, which is then broken off by hand. This procedure ensures greater safety for the patient and avoids any risk of damaging the medullary canal.

The cutting guide 1 having the distal surface 2d, the proximal surface 2p, and the height h, thus, the distance between the proximal surface 2p and the distal surface 2d, shaped according to the specific patient, allows the surgeon to cut the vertebrae following the natural course of the vertebrae and up to a pre-set depth.

The slots 3a and 4a have through planes across their longitudinal extension.

Depending on the degree of deformity to be treated, these through planes may be vertical and orthogonal to the frontal plane F and inclined with respect to the transverse plane T and with respect to the sagittal plane S to meet only in the lateral direction, i.e. to one side of the vertebral column, and usually on the side of the vertebra that does not support the guide. Otherwise, these planes may be inclined with respect to the frontal plane F and transverse plane T and orthogonal to the sagittal plane S, so as to converge only in the proximal direction, or be inclined with respect to the sagittal plane S, the frontal plane F, and the transverse plane T, and thus converge both in the lateral and in the proximal directions. In other words, the planes can only meet to the side of the vertebral column; or intersect in the proximal direction, thus, below the vertebral column; or in the volume defined by the vertebral column (depending on the inclination angle of the planes themselves), defining their respective cutting planes inclined in the back-front direction considering a patient in a prone position; or they can meet laterally and even lower down. In other words, the cutting through planes across the slots can intersect below the line of the vertebral column, again considering a patient in a prone position, either only laterally or both below the vertebral column as well as laterally.

Figure 5:
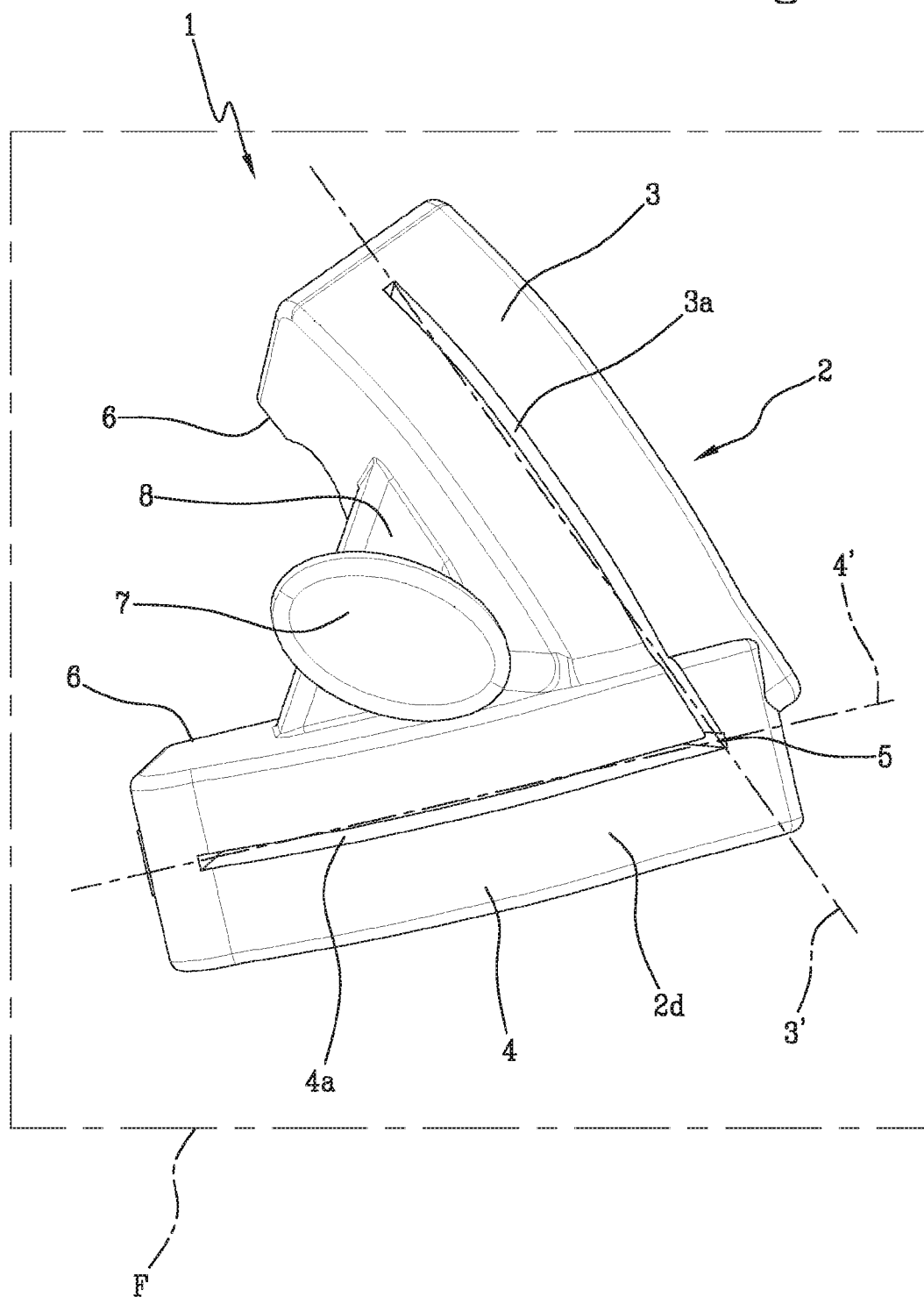
FIG. 5 is a view from above of the guide shown in FIG. 3.

As can be seen in FIG. 5, the cutting guide 1 has a substantially triangular plan shape, the arms 3 and 4 having a preferred spatial arrangement oriented along the longitudinal axes 3' and 4' inclined with respect to each other. This shape allows the surgeon, who has to keep the guide in position, to better divide the force they exert. These forces are better divided, distributing themselves evenly over the vertebrae that are being operated on.

In particular, the guide 1 comprises at least three supporting feet 6, at least one at each arm and one near the vertex 5. Depending on the vertebral column's degree of deformity, on the extension of the wedge portion to be removed, and on the angle defined by the longitudinal axes of symmetry 3' and 4' of the arms 3 and 4, there can be more than three supporting feet 6, for example, two at each arm (placed opposite to each other along the longitudinal extension of the arms themselves), and at least two interposed between the arms themselves, as can be seen in FIGS. 6 and 7.

To facilitate its gripping and holding in position, the guide 1 is provided with a gripping and positioning element 7.

This gripping and positioning element 7 is preferably interposed between the first 3 and the second 4 arm.

As can be seen in the attached figures, there is a connecting bridge 8 advantageously interposed between the first 3 and the second 4 arm.

The gripping and positioning element 7 is advantageously positioned at and above the connecting bridge 8, to allow the guide 1 to be gripped and held in the correct position during the cutting step.

The connecting bridge 8 can also have a triangular shape, with a vertex coinciding with the gripping and positioning element 7, so as to uniformly distribute the pressure force exerted by the surgeon when they press over the gripping element 7 (FIGS. 6 and 7).

The pressure that the surgeon exerts on the gripping element 7 is distributed over the entire guide 1 up to the supporting feet 6 thanks to the triangular configuration of the connecting bridge 8 and/or of the guide itself 1.

FIG. 1 shows a perspective view of the guide 1, joined to a portion of the vertebral column 100, in which the V-shape course of the slots 3a and 4a is clearly visible. The special V shape of the slots 3a and 4a and the triangular shape of the guide 1 is also easy to see in FIG. 5.

Figure 2:
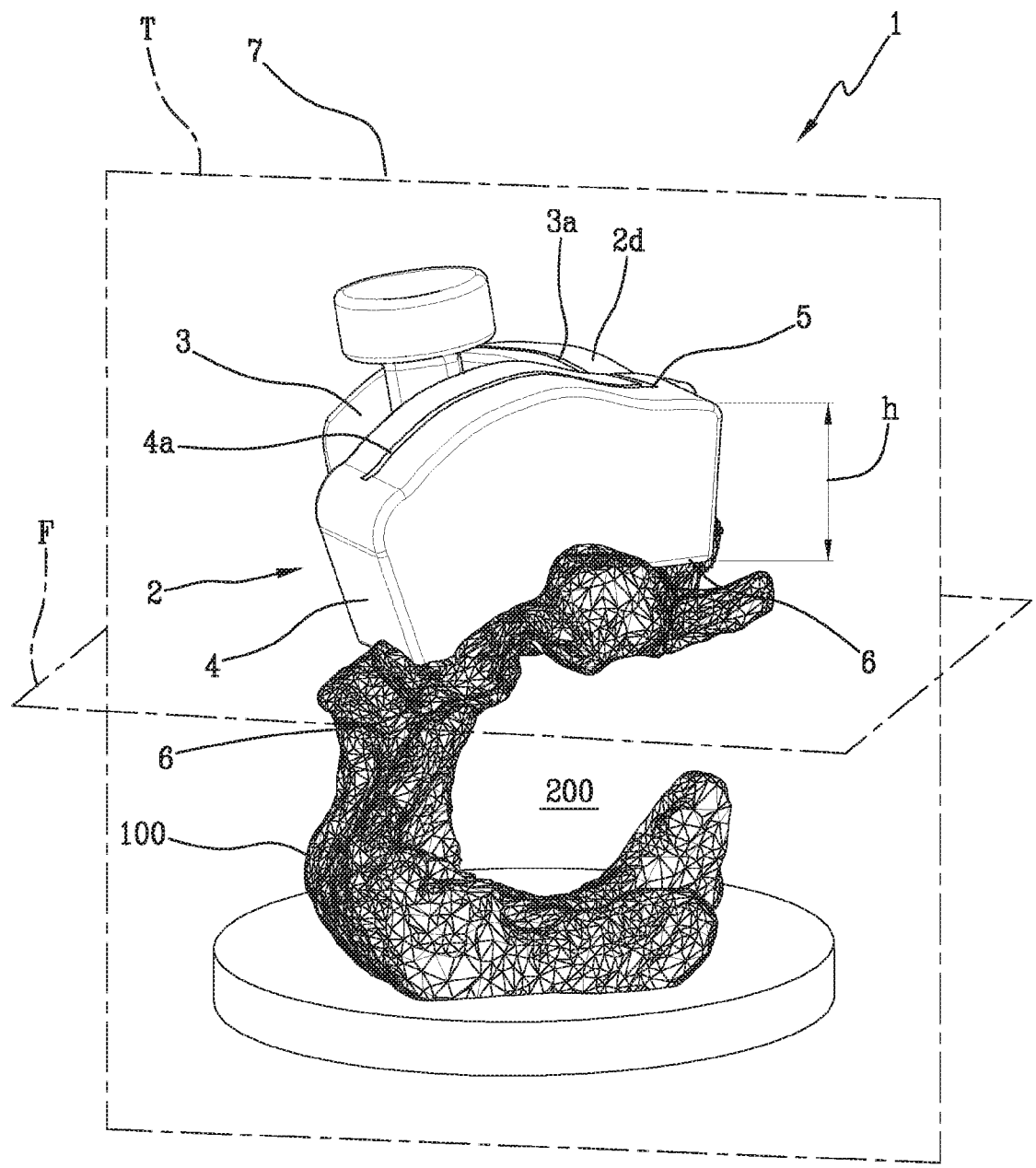
FIG. 2 is a lateral view of the cutting guide shown in FIG. 1.
Figure 3:
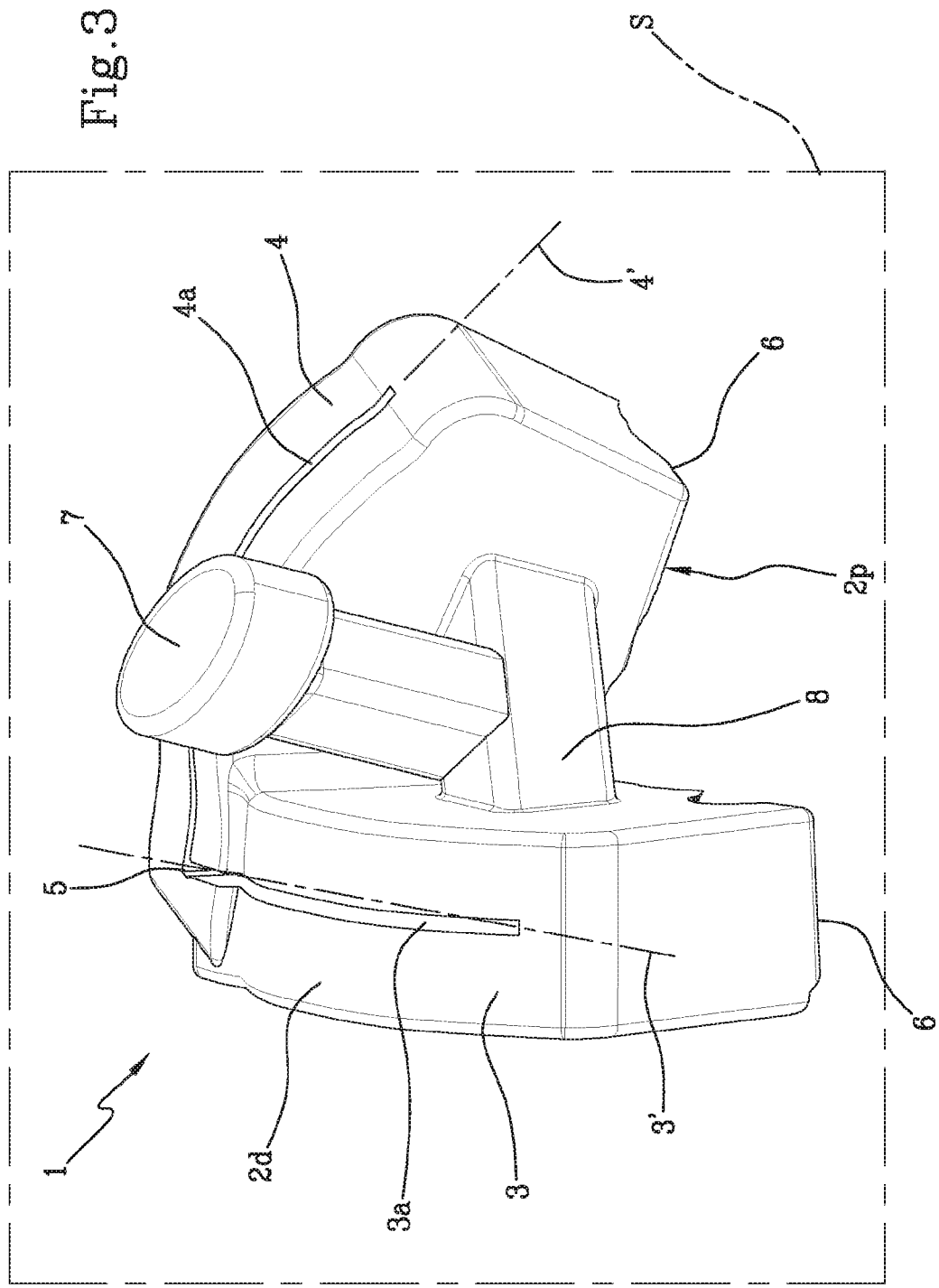
FIG. 3 is a perspective view of the cutting guide shown in FIG. 1, not joined to any vertebra.

Also in FIG. 2, the guide 1 is joined to the portion of the vertebral column 100 and is shown in a lateral position. In this way, not only the course of the proximal surface 2p, which is shaped according to the specific patient, but also the course of the distal surface 2d, which is also shaped according to the specific patient, can easily be seen. We note that both the distal surface 2d and the proximal surface 2p follow the course of the vertebra 100. The medullary canal 200 can also be seen in FIG. 2. The portion of the vertebral column 100 shown in FIGS. 1 and 2 is actually the result of the union of at least two vertebrae, since they are collapsed on each other as a result of spinal deformation. The operation is performed on several vertebrae, usually on two to four, depending on the width of the portion to be removed.

Figure 4:
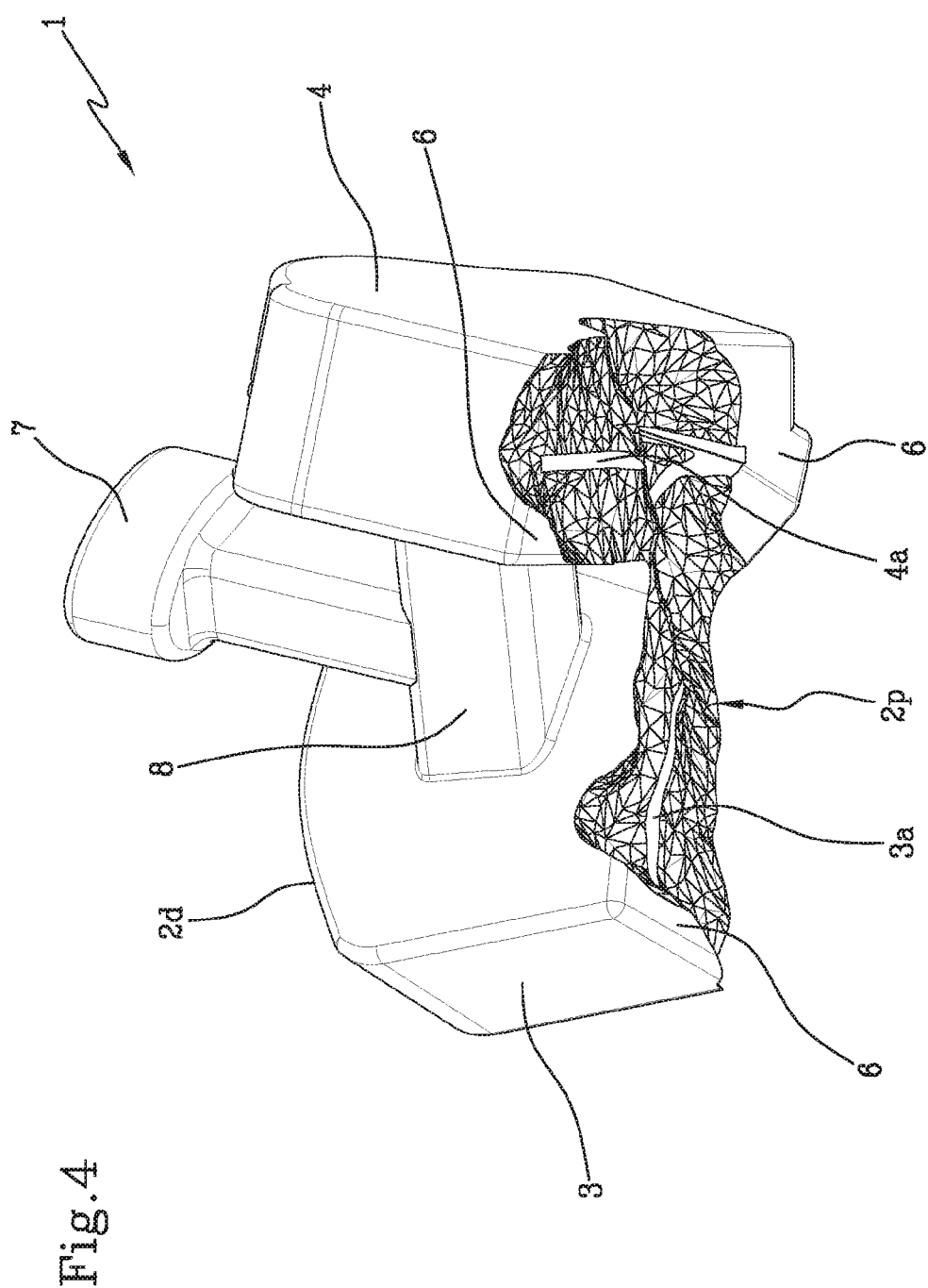
FIG. 4 is a perspective view of the bottom of the guide shown in FIG. 3.

FIG. 4 shows the proximal surface 2p in which the two slots 3a and 4a and the supporting feet 6 can be seen.

Finally, FIG. 5 clearly shows the triangular configuration of the guide 1 itself, while FIGS. 6 and 7 show the triangular shape of the connecting bridge 8 and a different angular arrangement of the arms 3 and 4.

In use, the cutting guide 1 is designed according to the specific anatomy of the patient in all its dimensions, specifically shaping itself to the proximal surface, the distal surface, and the height of the guide itself. Depending on the type of spinal deformation that the patient has, the inclination that the cutting planes must have is also planned in advance.

Again on the basis of the type of spinal deformation that the patient has, the operation is planned by preparing the cutting guide with the vertex 5, or, in any case, the virtual meeting point of the longitudinal axes of symmetry 3' and 4' of the arms 3 and 4, facing on one side or the other, and also defining the inclination of the cutting planes.

The cutting guide is positioned at the area of the vertebral column on which the operation is to be carried out, positioning it to rest on the specific feet, which are also shaped according to the anatomy of the patient in their lower surface, which will come into contact with the vertebrae.

The surgeon holds the guide 1 firmly in place by acting on the gripping and positioning element 7 and thus inserts the cutting blade inside the slots 3a and 4a, sawing the vertebrae up to a distance of a few millimetres, usually 0.5-1 mm, from the top of the medullary canal. In other words, the blade does not sink into the medullary canal to avoid the patient's suffering neurological damage.

The height of arms 3 and 4 of the cutting guide 1 is defined in the preoperative step according to the length of the cutting blade to be used.

Once the desired incision has been made, the blade is removed as well as the guide and the surgeon proceeds by manually breaking off the vertebra portion that has not been severed by the blade. The vertebrae are then manually realigned and locked in the desired position with special fastening devices.

The V cut is used to bring the vertebral column back to the correct morphology both on the coronal plane (frontal to the patient) and on the sagittal plane (lateral to the patient).

Compared to the applications known up until today, the guide that is the subject of the present invention enables osteotomy cuts to be performed, with the help of 3D planning, in a precise manner, perforating the bone at a predefined depth, according to the dimensions of the cutting blade.

The choice of contact zones is linked to the cutting planes planned for the osteotomy, but the width of the individual arms can be increased or decreased so as to ensure the guide's sufficient stability.

The cranial slots 3a and caudal slots 4a allow the cutting blade to be inserted to perform the resection of the bone to a pre-set depth and their width can be adapted depending on the dimensions of the blade used.

The gripping and positioning element 7 makes it easier to keep the guide in the correct position during its use and is positioned so as not to interfere with the cutting blade.

Once the guide has been made according to the anatomy of the specific patient, it is placed on the identified zone to remove the portion of the vertebral column that will comprise at least two vertebrae collapsed on top of each other.

The guide is held in place by means of the gripping and positioning element and the vertebrae are then resected by inserting the blade through each slot, following the natural course of the vertebrae in such a way as to reach a predefined cutting depth.

Subsequently, the sectioned wedge is manually removed, exerting a force to break off the last portion of bone that has purposefully not been sectioned.

Advantageously, the fulcrum where the two generators of the cutting lines are joined is inside the vertebra, since the cutting planes always intersect on the side of the vertebra that does not support the guide. If the inclination of the two planes in the distal-proximal direction is not very pronounced, the fulcrum is located below the vertebral column, considering a patient in a prone position. After having created the space necessary for the movement of the vertebral column, the spine is forced to re-assume an anatomical shape by straightening the deformed portions, bringing the sectioned and exposed surfaces closer together.

The bars are secured to the vertebral column with spinal screws to lock the vertebral column in its new position.

The main innovation is the ability to perform an osteotomy on the vertebral column, with cuts that are planned prior to the surgery, in a precise and safe way.

The guide allows to perform osteotomies even in the presence of severe deformities of the vertebral column.

The invention claimed is:

1. A cutting guide for spinal osteotomy comprising a main body having a first arm and a second arm, each arm defining a respective through slot, wherein the main body comprises a distal surface and a proximal surface, the proximal surface being shaped according to an anatomy of a specific patient.

2. The cutting guide according to claim 1, wherein the cutting guide has a height as measured between the distal surface and the proximal surface, wherein the height is shaped according to the anatomy of the specific patient.

3. The cutting guide according to claim 1, wherein said first arm faces a cranial direction when in use, and said second arm faces a caudal direction when in use, wherein each arm extends along a main longitudinal development direction along respective axes of symmetry inclined with respect to each other.

4. The cutting guide according to claim 3, wherein said slots develop along the longitudinal axes of symmetry of the respective first and second arms.

5. The cutting guide according to claim 4, wherein said slots have a respective plane passing through the longitudinal extension thereof said planes intersecting laterally with respect to said guide, and therefore laterally with respect to a vertebral column of the patient when in use.

6. The cutting guide according to claim 5, wherein said planes converge in a proximal direction and intersect below the proximal surface.

7. The cutting guide according to claim 1, wherein the cutting guide has a triangular plan shape.

8. The cutting guide according to claim 7, wherein the cutting guide comprises at least three supporting feet, wherein each arm comprises at least one of the supporting feet.

9. The cutting guide according to claim 8, wherein the cutting guide comprises a gripping and positioning element.

10. The cutting guide according to claim 9, wherein said gripping and positioning element is interposed between said first and said second arm.

11. The cutting guide according to claim 10, wherein the cutting guide comprises a connecting bridge between said first and said second arm, said gripping and positioning element being positioned at said connecting bridge.

12. The cutting guide according to claim 11, wherein said connecting bridge has a substantially triangular shape with a vertex coinciding with the gripping and positioning element.

* * * * *